(12) United States Patent
Matsutani et al.

(10) Patent No.: US 7,648,516 B2
(45) Date of Patent: Jan. 19, 2010

(54) MEDICAL KNIFE

(75) Inventors: Kanji Matsutani, Tochigi-ken (JP);
Takashi Ina, Tochigi-ken (JP);
Masahiko Saito, Tochigi-ken (JP);
Takayuki Matsumoto, Tochigi-ken (JP)

(73) Assignee: Mani, Inc., Tochigi-ken (JP)

( * ) Notice: Subject to any disclaimer, the term of this patent is extended or adjusted under 35 U.S.C. 154(b) by 947 days.

(21) Appl. No.: 10/874,249

(22) Filed: Jun. 24, 2004

(65) Prior Publication Data

US 2005/0004587 A1 Jan. 6, 2005

(30) Foreign Application Priority Data

Jun. 25, 2003 (JP) ............................. 2003-180614

(51) Int. Cl.
*A61B 17/32* (2006.01)

(52) U.S. Cl. ....................................... 606/167; 606/166

(58) Field of Classification Search .................. 606/166, 606/167, 107, 181, 183, 185, 170, 174
See application file for complete search history.

(56) References Cited

U.S. PATENT DOCUMENTS 5,352,233 A * 10/1994 Anis .......................... 606/167
5,713,915 A * 2/1998 Van Heugten et al. ....... 606/167
6,120,518 A 9/2000 Mark et al.
6,554,840 B2 * 4/2003 Matsutani et al. ........... 606/107
2002/0026205 A1 2/2002 Matsutani et al.

OTHER PUBLICATIONS

Patent Abstracts of Japan, vol. 2000, No. 20, Jul. 10, 2001 & JP 2001 057980 A, Mar. 6, 2001 & Abstract.

* cited by examiner

*Primary Examiner*—Kevin T Truong
(74) *Attorney, Agent, or Firm*—Townsend & Banta

(57) ABSTRACT

A medical knife has a cutting edge formed along the outer edge of a blade portion, and the thickness of the lower portion located under a boundary acting as a surface including the cutting edge is made thinner than that of an upper portion located on the boundary, or a lower surface is composed of the surface including the cutting edge. The surface of the upper portion on the above surface including the cutting edge is composed of a first slanting surface constituting the cutting edge, a second reflecting surface, and a flat surface composed of a non-reflecting surface as well as the lower portion has a lower slanting surface 10 and a lower flat surface 11 each composed of a reflecting surface. With the above arrangement, the medical knife can reduce the amount of reflected light when an operation such as an ophthalmic operation is executed under a microscope.

4 Claims, 6 Drawing Sheets

FIG.6

MEDICAL KNIFE

BACKGROUND OF THE INVENTION

1. Field of the Invention

The present invention relates to a medical knife which prevents a doctor from feeling the glare of illumination light used in an operation by reducing the reflection of the light as well as prevents deterioration of the cutting quality of the knife in the operation.

2. Description of the Related Art

Microscopic operations represented by an ophthalmic operation are basically executed by observing an affected area while enlarging it under a microscope. In this case, a problem arises in that it is difficult for a doctor to execute the operation because the light, which illuminates the affected area, is reflected on the surface of a medical knife and makes it difficult for the doctor to observe the affected area. To solve the above problem, there has been provided a medical knife which permits a doctor to easily observe an affected area by composing the entire surface of the knife of a non-reflecting surface. The non-reflecting surface is composed of a surface on which fine concavities and convexities are formed so that the light, which is directly reflected to the eyes of the doctor, can be suppressed by diffusely reflecting the light. In the medical knife arranged as described above, however, when the knife pierces living body tissue, friction is increased between the concavities and the convexities and the living body tissue, and further a problem also arises in that the sharpness of the knife for dissecting the living body tissue is lost because concavities and convexities are also formed on a cutting edge, and thus the cutting quality of the knife is deteriorated. When the cutting quality is deteriorated, it is difficult for an operator to form an incision wound which in agreement with his or her image, that is, it is difficult for the operator to form an incision wound having a self-closing property for permitting the incision wound to close by itself. This may adversely affect the curing of the incision wound after the operation.

Under the above circumstances, generally doctors select a medical knife depending on whether they put high priority on the cutting quality of the knife by enduring reflection of light or put high priority on reduction of reflected light by enduring deterioration of the cutting quality of the knife.

To solve the above problem, there has been proposed surgical knives whose surface, which is caught in a field of view when they are used in an operation under a microscope, is composed of a portion subjected to a reflection preventing treatment and a portion not subjected to the treatment (for example, refer to Japanese Patent Application Laid-Open (JP-A) No. 2001-57980). In the above surgical knives, the lower surface of a cutting edge formed around the periphery of the knife is entirely subjected to the reflection preventing treatment except a slanting surface constituting the cutting edge, and the upper surface of the cutting edge is composed of a slanting surface constituting the cutting edge and a roughly ground surface formed along the slanting surface constituting the cutting edge inwardly of it, and a central flat surface, which continues to the inside and the back side of the roughly ground surface and is composed of a surface subjected to the reflection preventing treatment.

In the knives according to the art disclosed in JP-A No. 2001-57980, since only the slanting surface constituting the cutting edge is composed of the reflecting surface, no light is reflected from the surfaces other than the slanting surface constituting the cutting edge. Accordingly, a workload on a doctor can be reduced because the amount of light, which is reflected when an affected area is dissected, is reduced. However, even the knives arranged as described above are not yet perfect, and it has been required to develop a medical knife which reduces an amount of reflected light and has excellent cutting quality.

SUMMARY OF THE INVENTION

Accordingly, an object of the present invention is to provide a medical knife that can reduce an amount of light reflected in an operation as well as secure excellent cutting quality.

To solve the above problems, a medical knife according to the present invention includes: a cutting edge formed along the outer edge of a blade portion; a virtual surface including the cutting edge; a surface of an upper portion which is composed of a blade surface constituting the cutting edge and a molded surface formed of a non-reflecting surface and located on a boundary acting as the virtual surface including the cutting edge; and a surface, which is composed of a reflecting surface, of a lower portion located under the boundary acting as the virtual surface including the cutting edge with the thickness of the lower portion made thinner than that of the upper portion.

In the medical knife, the cutting edge is formed along the outer edge of the blade portion, and the thickness of the lower portion located under the boundary, which acts as the virtual surface including the cutting edge, is made thinner than that of the upper portion located on the boundary. In the medical knife arranged as described above, when the tip of the blade portion of the knife pierces an affected area and is pushed thereinto in a lengthwise direction, it advances so as to move from the upper portion side to the lower portion side.

Accordingly, the surface of the lower portion, which is located under the boundary acting as the surface including the cutting edge, is pressed against the tissue of a patient, and the surface of the upper portion is spaced apart from the tissue of the patient. As a result, it is possible to reduce a friction resistance between the knife and the patient as well as to reduce the value of a total friction resistance including the friction resistance between the surface of the upper portion and the patient by composing the surface of the lower portion of the reflecting surface.

That is, the cutting quality of the medical knife is determined by a combination of an incision resistance when tissue is dissected with the cutting edge of the knife and a friction resistance when the knife passes through the tissue. The incision resistance is affected by a degree of sharpness of the cutting edge, and the friction resistance is affected by smoothness of the medical knife. Thus, it is necessary to reduce the incision resistance and the friction resistance to enhance cutting quality in its entirety.

Therefore, the cutting quality of the medical knife can be enhanced in its entirety by reducing the amount of reflected light incident on a doctor by composing the surface of the upper portion, which faces the doctor in an operation, of the non-reflecting surface and by reducing the friction resistance by composing the surface of the lower portion of the reflecting surface (smooth surface).

DESCRIPTION OF THE PREFERRED EMBODIMENTS

A medical knife according to the present invention permits an operation to be executed easily by reducing the glare, which is felt by a doctor, of illumination light irradiated to a patient in the operation by reducing an amount of the light reflected on the surface thereof as well as prevents deterioration of the cutting quality thereof by suppressing an increase of a resistance when an affected area is dissected with the knife.

Accordingly, a large area, which faces a doctor, of the medical knife according to the present invention is composed of a non-reflecting surface for reflecting light diffusely and the surface thereof which does not face the doctor is composed of a smooth surface to thereby reduce a friction resistance generated between the knife and tissue.

In particular, the medical knife according to the present invention has a function for piercing an affected area, for example, an eyeball and the like, forming an initial incision wound, dissecting the affected area along living body tissue from the initial incision wound as a start point, and broadening the affected area while pressing it and a function for forming an incision wound having a self-closing property which permits the incision wound to close by itself. Accordingly, the medical knife can be advantageously employed as a knife for eye clinic which is used to dissect a cornea, and a portion between the cornea and a sclera in an ophthalmic operation. However, the present invention is by no means limited to a knife having a particular use and can be advantageously applied to medical knives for piercing, dissecting, and cutting off an affected area which must be microscopically manipulated under a microscope in a brain operation and the like.

Although the medical knife is formed in a flat shape, the flat shape is not standardized. More specifically, a typical flat shape includes an approximately diamond shape having a sharp tip at the extreme end thereof and a shape having a curved extreme end. However, the flat shape of the medical knife according to the present invention is not limited, and a medical knife whose flat shape is formed in, for example, a trapezoidal flat shape with its extreme end formed flat and its dimension increasing toward both the sides thereof from the flat portion, and the like are also included in the medical knife of the present invention.

Further, the lateral sectional shape of the medical knife is not standardized, and the medical knife is arranged such that the thickness of the lower portion thereof under a boundary, which acts as a surface including a cutting edge formed along the outer edge of a blade portion formed at the extreme end of the knife, is smaller than the thickness of the upper portion thereof on the boundary. That is, since the thickness of the upper portion of the medical knife on the boundary is made thicker than the thickness of the lower portion thereof under the boundary, when the knife linearly pierces an affected area, the knife slides so as to be pressed downward through the piercing motion thereof, thereby it is possible to reduce the pressure applied by the tissue to the surface of the upper portion of the knife.

Although the thickness of the lower portion of the knife under the boundary, which is composed of the surface including the cutting edge, must be smaller than that of the upper portion thereof on the boundary, the thickness values of these portions are not limited. That is, the surface of the medical knife below the boundary may be spaced apart from the boundary or may be in coincidence with the boundary. When the surface of the medical knife below the boundary is in coincidence with the boundary, the surface including the cutting edge constitutes the lower surface of the knife.

When, for example, blade surfaces, which constitute a cutting edge, are formed in the upper and lower portions of a knife located on and under a boundary acting as a surface including the cutting edge, the thickness of the upper portion is preferably within the range of 55% to 99% of the overall thickness of the knife (which is a total thickness obtained by adding the thickness of the upper portion and the thickness of the lower portion), and, in particular, more preferably within the range of 75% to 99% of the overall thickness.

In the present invention, the surface of the upper portion on the boundary, which is composed of the surface including the cutting edge, is composed of a non-reflecting surface, and the surface of the lower portion under the boundary is composed of a reflecting surface. The surface of the upper portion is composed of a blade surface constituting the cutting edge and a molded surface other than the blade surface, and the molded surface is composed of the non-reflecting surface. Accordingly, the blade surface constituting the cutting edge is composed of a surface other than the non-reflecting surface, that is, is composed of a reflecting surface.

The non-reflecting surface is preferably a surface which can diffusely reflect irradiated light. A method of forming the non-reflecting surface includes a method of forming an infinite number of concavities and convexities only on a selected portion of a molded surface by blowing fine particles to the selected portion (sand blast), a method of making the molded surface rough by erosion executed by chemical polishing and electrolytic polishing, and the like. It is preferable to select and employ a most reasonable method from these treatment methods in consideration of a material constituting the medical knife. When, for example, the material is martensitic stainless steel, the concavities and the convexities can be formed by the chemical polishing and the electrolytic polishing, and when the material is austenitic stainless steel, they can be formed by the sand blast.

Since the non-reflecting surface is formed only on one side of the knife, i.e. only on the upper portion thereof, no treatment is applied to the lower portion, which must not be subjected to the above treatment, or masking is made to the lower portion by any method. When, for example, only the one side is subjected to the sand blast treatment, it is executed by disposing a blast gun only on the one side, and when it is subjected to the chemical polishing or the electrolytic polishing, lower and upper slanting surfaces, and the like which are not subjected to the treatment, are masked.

The reflecting surfaces of the lower and upper portions, which are located under and on the boundary including the cutting edge and constitute the blade surfaces constituting the cutting edge, are composed of smooth surfaces. It is preferable that the reflecting surfaces be not subjected to a special treatment as the reflecting surfaces and that the surfaces, which are formed as the finished surfaces of the medical knife, be used as the reflecting surfaces as they are.

The material, which constitutes the medical knife according to the present invention, is not particularly limited. However, it is preferable that the material be composed of stainless steel in consideration of rustproof and easiness of processing, and, in particular, it is preferable that the stainless steel be composed of austenitic stainless steel.

Figure 1:
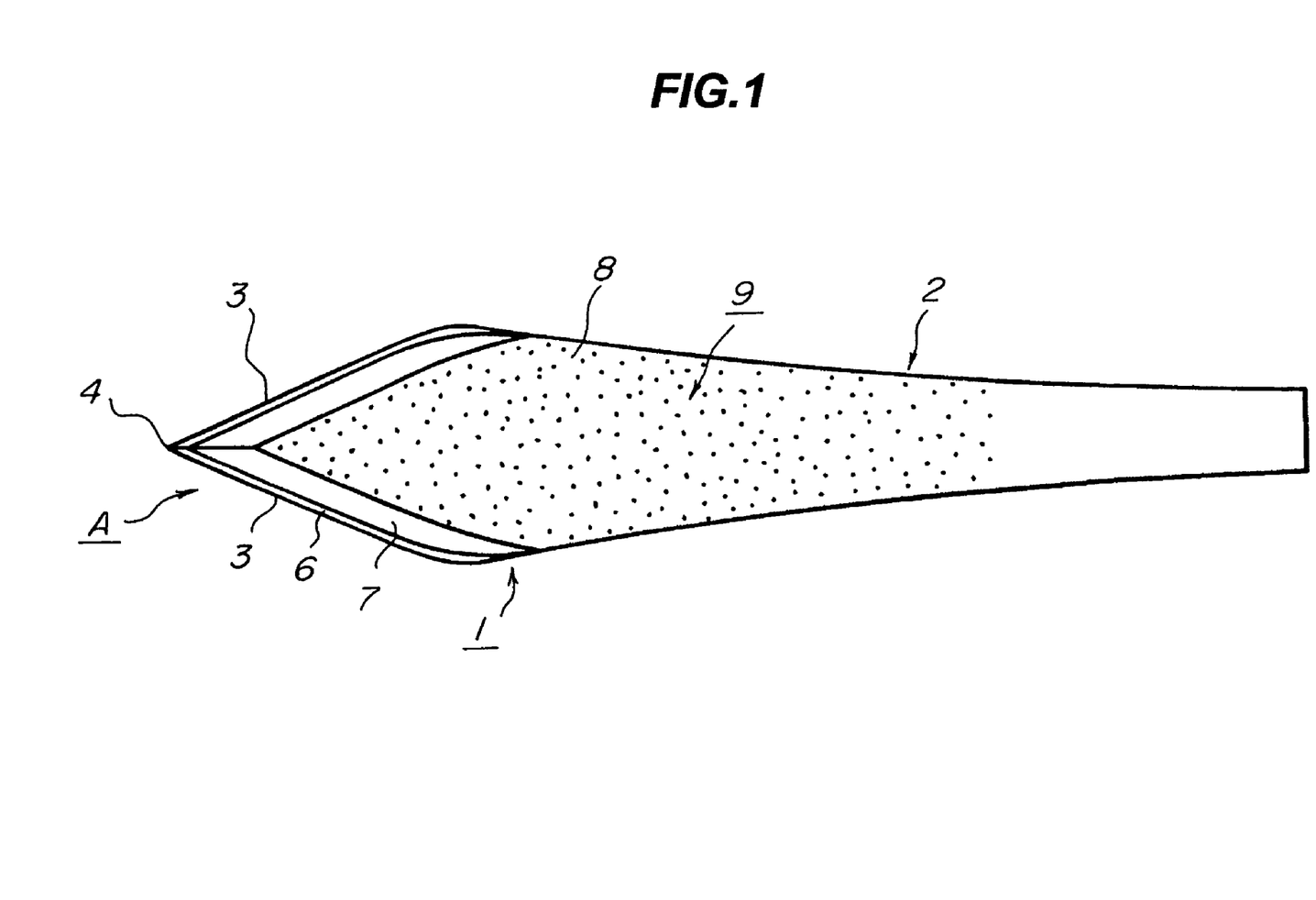
FIG. 1 is a plan view explaining a flat shape of a knife having a sharp tip.
Figure 2:
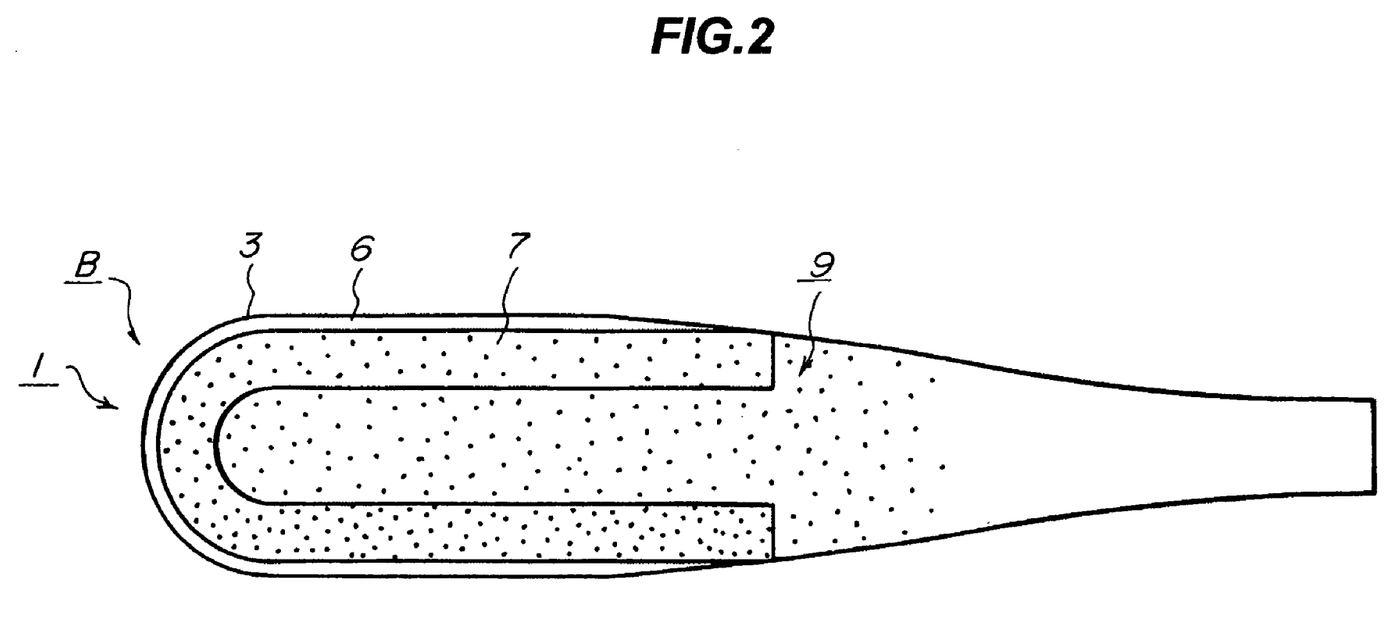
FIG. 2 is a plan view of a knife whose tip is formed in a curved state.
Figure 3:
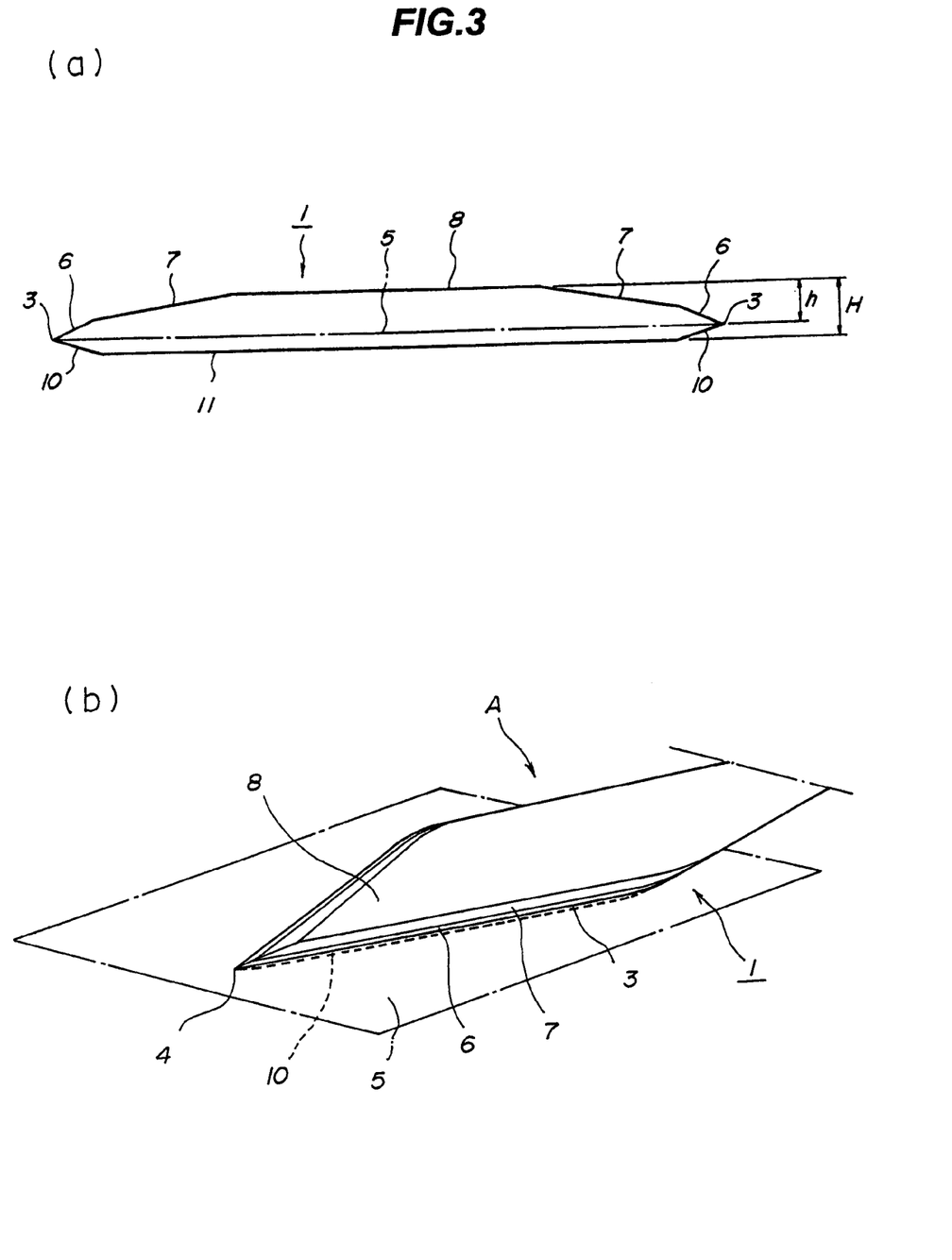
FIG. 3A is a lateral sectional view of a knife according to a first embodiment.
FIG. 3B is a view explaining the relationship between a surface including a cutting edge and acting as a virtual surface and a blade portion 1 of knives A and B.
Figure 4:
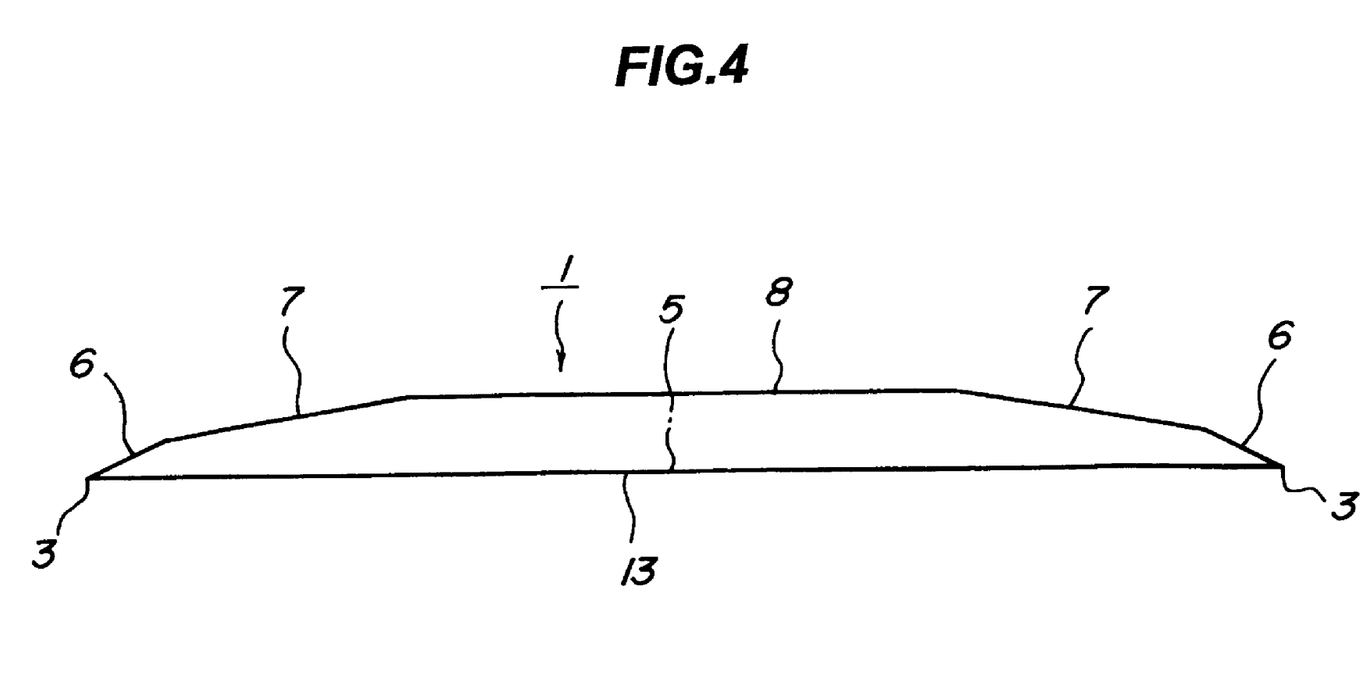
FIG. 4 is a lateral sectional view of a knife according to a second embodiment.
Figure 5:
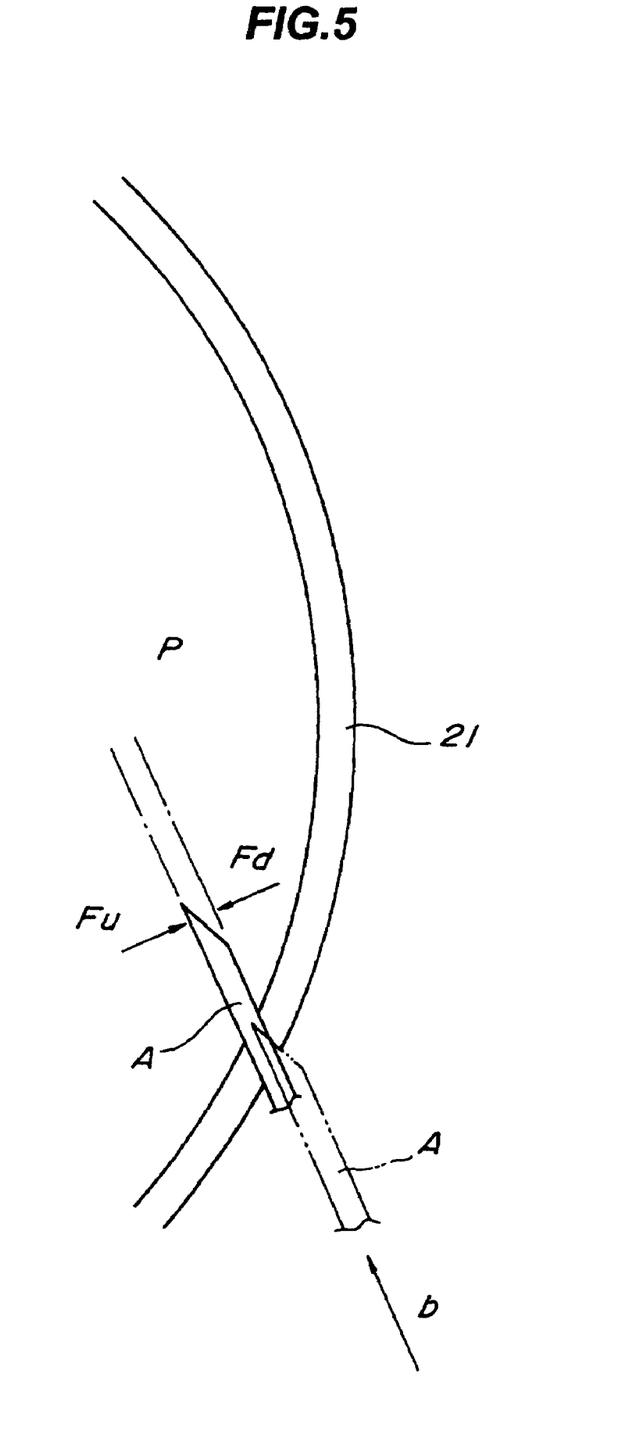
FIG. 5 is a view explaining a behavior of the knife according to the first embodiment when an affected area is dissected with the knife.
Figure 6:
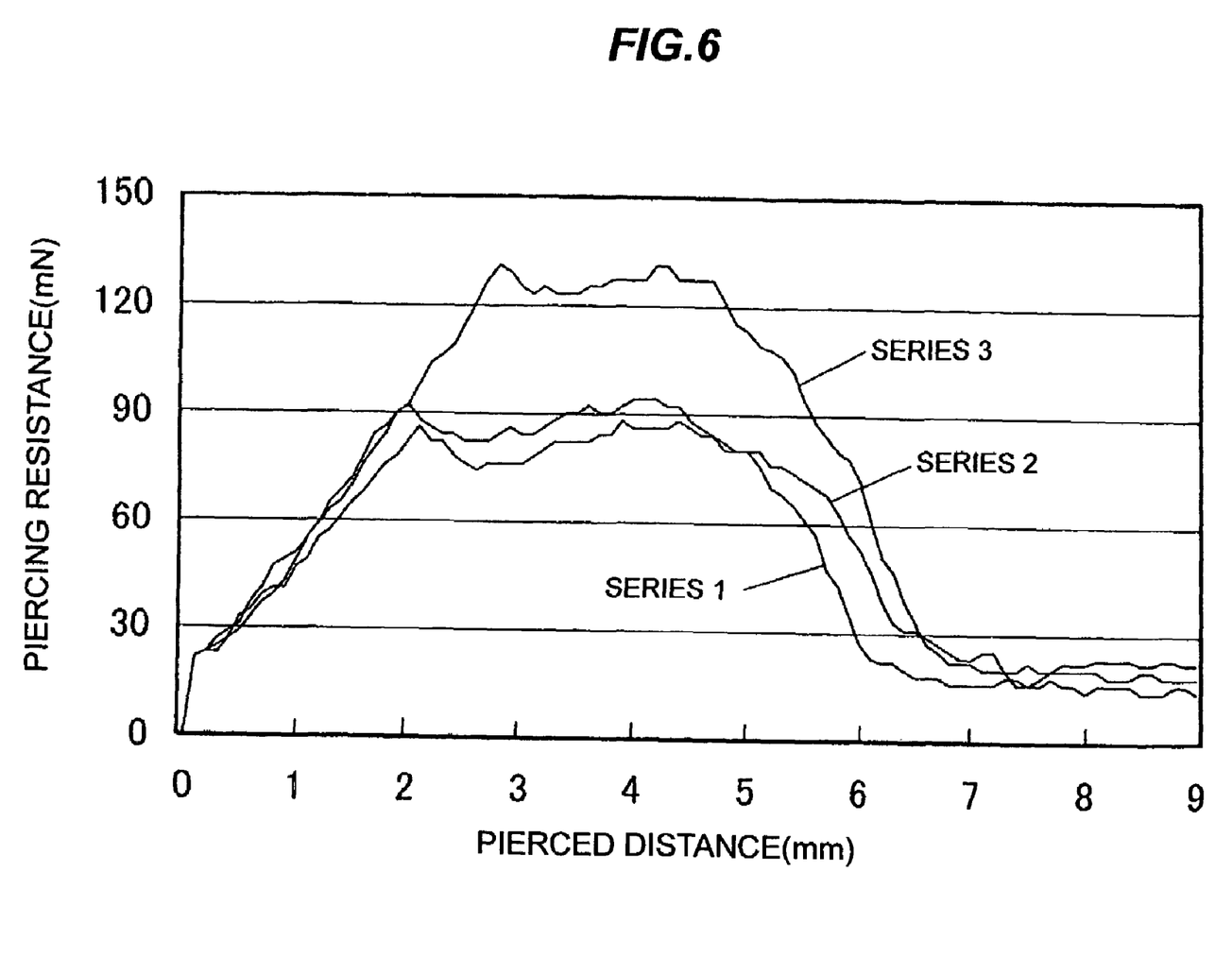
FIG. 6 is a graph showing a result of an experiment for comparing the piercing resistance of the knife according to the first embodiment with that of a conventional knife.

Preferable embodiments of the above medical knife when it is applied to a knife used in an ophthalmic operation will be explained below with reference to figures. FIG. 1 is a plan view explaining a flat shape of a knife having a sharp tip. FIG. 2 is a plan view of a knife whose tip is formed in a curved state. FIG. 3 is a lateral sectional view of a knife according to a first embodiment. FIG. 4 is a lateral sectional view of a knife according to a second embodiment. FIG. 5 is a view explaining a behavior of the knife according to the first embodiment when an affected area is dissected with the knife. FIG. 6 is a graph showing a result of an experiment for comparing the piercing resistance of the knife according to the first embodiment with that of a conventional knife.

First, the flat shape of the knife will be explained with reference to FIGS. 1 and 2. In the present invention, the flat shape and the sectional shape of the knife are not standardized, and there are a knife A whose flat shape is formed in an approximately diamond shape having a sharp tip at the extreme end thereof as shown in FIG. 1 and a knife B whose flat shape at the extreme end thereof is formed in a curved shape as shown in FIG. 2 as knives having a typical shape. However, the medical knife according to the present invention is not limited to the flat shape, and a medical knife whose flat shape is formed in a trapezoidal flat shape with its extreme end formed flat and its dimension increasing toward both the sides thereof, and the like are also included in the medical knife of the present invention.

As shown in FIGS. 3 and 4, there are provided the knives A and B the shape of the lateral cross sections of which is formed such that the upper portion thereof on a boundary acting as a surface (virtual surface) 5 including a cutting edge 3, which will be described later, and the lower portion thereof under the boundary are formed to have a different thickness, and further there are provided the knives A and B whose lower portions themselves have a different thickness. More specifically, there are provided the knives A and B whose upper and lower portions on and under the boundary have a different thickness as well as whose lower portions has a different thickness.

First, an arrangement of the knife A will be explained with reference to FIG. 1. In FIG. 1, the knife A has a blade portion 1 and a shank 2 formed continuously to the blade portion 1. The knife A is formed to have a sharp tip 4 at the extreme end thereof, and the cutting edge 3, which has a function as a cutting blade, is formed from the tip 4 along the outer edge of the blade portion 1 on both the sides thereof.

A plurality of surfaces are formed on the upper and lower portions on and under a surface 5 including the cutting edge 3 formed along the outer edge of the blade portion 1, respectively. That is, a first slanting surface 6, which constitutes the cutting edge 3, is formed on the upper portion on the cutting edge 3, and a second slanting surface 7 and a flat surface 8 are formed continuously to the first slanting surface 6.

Although the blade surface that constitutes the cutting edge 3 is mainly composed of the first slanting surface 6, it may be composed of the first slanting surface 6 and the second slanting surface 7. Accordingly, when the cutting edge 3 is composed of the first slanting surface 6, the second slanting surface 7 and the flat surface 8 are composed of a molded surface, and when the cutting edge 3 is composed of the first slanting surface 6 and the second slanting surface 7, the flat surface 8 is composed of the molded surface.

That is, the range, in which a non-reflecting surface is processed, includes the second slanting surface 7 and the flat surface 8 except the first slanting surface 6, or the flat surface 8. Further, the range may include the second slanting surface 7 and a portion of the flat surface 8, for example, up to the maximum width portion thereof depending on a method of using the medical knife.

The molded surface is composed of the non-reflecting surface on which an infinite number of concavities and convexities 9 are formed. In the embodiment, the infinite number of concavities and convexities 9 which constitute the non-reflecting surface are formed by sand blast.

When the sandblast is executed, green carborundum (GC), carborundum (C), white alundum (WA), alundum (A) and the like are used as a blast member (abrasive grains), and any of them may be preferably used. Further, it is preferable to select a grain size of the abrasive grains from the range of #600 to #1500 in consideration of a use (portion where they are used), a degree of reflection, and the like.

Further, a step, at which the sand blast is executed in a process for manufacturing the knife A, is not particularly limited. For example, it is possible to execute the sand blast after the knife is roughly molded, next, to polish the cutting edge, and then to execute an electrolysis treatment for removing burrs, it is also possible to execute the sand blast and the electrolysis after the cutting edge is polished, and further it is also possible to execute the sand blast after the second slanting surface 7 is formed to a raw material, and further to process the first slanting surface 6 and to subject it to the electrolysis treatment. Note that the electrolysis treatment also has an effect of putting the cutting edge and the surfaces in order and to remove the abrasive grains forced into the knife by the sand blast from the surface thereof.

An arrangement of the knife B will be explained with reference to FIG. 2. In FIG. 2, the same portions of the knife B as those of the knife A and the portions of the knife B which have the same functions as those of the knife A are denoted by the same reference numerals, and the explanation thereof is omitted.

As shown in the figure, although the flat shape of the knife B is somewhat different from that of the knife A, the knife B has substantially the same function and the same structure as those of the knife A except that the extreme end of the knife B is formed in a curved state in contrast to that the extreme end of the knife A is composed of the acute tip 4. Accordingly, the knife B has a first slanting surface 6, a second slanting surface 7 and a flat surface 8 formed in the upper portion thereof on a boundary acting as the surface 5 including the cutting edge 3, and the second slanting surface 7 and the flat surface 8, or the flat surface 8 is composed of a non-reflecting surface on which an infinite number of concavities and convexities 9 are formed.

A first embodiment of the shapes of the lateral cross sections of the knives A and B will be explained with reference to FIGS. 3A and 3B (since both the knives A and B are substantially the same knife, the shape of the lateral cross section of the knife A will be explained so as to represent both the knives A and B). As shown in FIG. 3A, the first slanting surface 6, the second slanting surface 7, and the flat surface 8 are formed on the upper portion of the knife A on a boundary acting as the surface 5 including the cutting edge 3, a lower slanting surface 10 for constituting the cutting edge 3 is formed on the lower portion of the knife A under the surface 5, and a lower flat surface 11 is formed continuously to the lower slanting surface 10. Further, FIG. 5B explains the relationship between the surface 5 including the cutting edge and acting as a virtual surface and the blade portion 1 of the knives A and B.

The lower slanting surface 10 and the lower flat surface 11 are composed of a reflecting surface, respectively. That is, the lower slanting surface 10 and the lower flat surface 11 are composed of a smooth surface so that even if they are caused to slide in living body tissue while pressing it, a friction resistance generated thereby is small.

When the dimension of the knife A from the flat surface 8 to the lower flat surface 11, which represents the overall thickness of the knife A, is shown by H, and the dimension of the knife A from the surface 5 including the cutting edge 3 to the surface 8 on one side of the knife A, which represents the thickness of the upper portion of the knife A on the boundary acting as the surface 5, is shown by h, the dimension h is set larger than one half the dimension H. Although the ratio h/H is not particularly limited, it is preferably within the range from 55% to 99% and more preferably within the range from 75% to 99% as described above.

As described above, the upper portion and the lower portion of the blade portion 1 are defined on and under the boundary acting as the surface 5 as the virtual surface including the cutting edge 3, and the thickness of the lower portion is made thinner than that of the upper portion. Accordingly, when the knife A pierces, for example, the cornea 21 of an eyeball as shown in FIG. 5, the knife A can be moved downward of a direction in which it is pierced. More specifically, since different force is generated on the upper surface and the lower surface of the knife A by intraocular pressure p acting when the cornea 21 is dissected (downward force Fd acting on the upper portion of the knife A is smaller than upward force Fu acting on the lower portion thereof), the knife A is offset downward in its entirety as it is pierced.

Accordingly, the knife A is in contact with the living body tissue such that the knife A weakly comes into contact with it on surfaces of the upper portion (the first slanting surface 6 to the flat surface 8) thereof and is pressed against the living body tissue on the surface of the lower portion (the lower slanting surface 10 and the lower flat surface 11) thereof. That is, the surface pressure acting on the surface of the upper portion is lager than the surface pressure acting on the surface of the lower portion. Since the surface of the lower portion is composed of the reflecting surface, the surface has a small friction coefficient, thereby the friction resistance, which is generated when the knife A is pierced, is not increased. Further, since the surface of the upper portion has the small surface pressure, the concavities and the convexities that constitute the non-reflecting surface are forced into the tissue, thereby the area of the concavities and the convexities which is in contact with the tissue can be reduced.

As described above, in the knife A, in which the thickness of the lower portion under the boundary acting as the surface 5 including the cutting edge 3 is smaller than that of the upper portion on the boundary as well as the surface of the upper portion is composed of the non-reflecting surface, a resistance generated when the knife A pierces living body tissue is somewhat larger than that of a knife whose entire surface is composed of a reflecting surface. However, the resistance of the knife A is sufficiently smaller than that of a knife whose entire surface is composed of a non-reflecting surface as well as an operation can be smoothly executed with the knife A because the amount of reflected light incident on a doctor can be reduced. Note that the doctor scarcely uses the knife A in an inverted state in an operation.

The inventors of the present invention executed an experiment for comparing the cutting qualities of a conventional knife whose entire surface was composed of a reflecting surface, a conventional knife whose entire surface was composed of a non-reflecting surface, and the knife of the present invention. The experiment was executed in such a manner that the corneas of pig's eyeballs were fixed on a jig, the corneas were vertically pierced with the knives, and the relationship between the pierced distance and the piercing resistance of each of the knives was measured. Although the thickness of the pig's corneas was about 0.9 mm and was larger than the thickness (about 0.5 mm) of a human cornea, the piercing resistance was approximately the same as the piercing resistance which was actually felt by an operator in an operation. FIG. 6 shows a result of the experiment. In FIG. 6, the line of a series 1 shows the measured value of the conventional knife whose upper and lower surfaces are entirely composed of the reflecting surface, the line of a series 2 shows the measured value of the knife A according to the present invention, and the line of a series 3 shows the measured value of the conventional knife whose upper and lower surfaces are entirely composed of the non-reflecting surface.

The following points are found as a result of the experiment. That is, when the pierced distance is within the range of 0 mm to about 2 mm, no significant difference occurs. However, when the pierced distance exceeds about 2 mm, a significant difference occurs. The difference is such that approximately the same piercing resistance is generated by the knife whose entire surface is composed of the reflecting surface and by the knife of the present invention, and a piercing resistance about 130% as large as the piercing resistance of the knife of the present invention is generated by the knife whose entire surface is composed the non-reflecting surface. The above tendency continues to the range in which the pierced distance reaches about 5 mm, and when the pierced distance exceeds about 5 mm, the piercing resistance of the knife of the present invention becomes larger than that of the knife whose entire surface is composed of the reflecting surface. However, the piercing resistance at the time is smaller than the piercing resistance of the knife whose entire surface is composed of the non-reflecting surface.

As described above, the knife A of the present invention can exhibit a performance that is approximately the same as the piercing resistance of the knife whose entire surface is composed of the non-reflecting surface. Further, the knife A of the present invention can exhibit a function for reducing reflected light in a degree similar to that of the knife whose entire surface is composed of the non-reflecting surface when the light reflected on a doctor by the knife of the present invention is compared with that reflected on a doctor by the above knife.

A second embodiment of the shape of other lateral cross section of the knife A will be explained with reference to FIG. 4. As shown in FIG. 4, a lower surface 13 is formed in coincidence with a surface 5 including a cutting edge 3 under the surface 5. Even in the knife A arranged as described above, when the knife A pierces living body tissue, it is moved downward likewise the first embodiment and can exhibit the same effect as that of the knife A having the cross section shown in FIG. 3.

As described above in detail, the medical knife according to the present invention can reduce the amount of reflected light incident on a doctor in an operation executed under a microscope as well as can secure excellent cutting quality. Accordingly, a microscopic operation can be executed easily and securely with medical knife.

What is claimed is:

1. A medical knife which is formed in a diamond shape in plan view having a sharp tip at the extreme end thereof and having a function of forming an incision wound having a self-closing property which permits the incision wound to close by itself, comprising:
(A) a shank; and
(B) a blade portion formed continuously to the shank, said blade portion comprising:
(b) an upper portion having:
 (i) a first slanting surface,
 (ii) a second slanting surface formed continuously with the first slanting surface, and
 (iii) a non-reflective surface formed adjacent the second slanting surface, said non-reflective surface having a plurality of concavities and convexities formed therein and being formed in a whole diamond shape in plan view; and
 (iv) a cutting edge formed adjacent the first slanting surface of the upper portion, along an outer edge of the blade portion, said cutting edge defining a virtual surface;
(c) a lower portion formed adjacent the cutting edge and under the virtual surface formed thereby, opposite the upper portion, having:
 (i) a reflective lower slanting surface formed adjacent the cutting edge; and
 (ii) a reflective lower surface formed adjacent the reflective lower slanting surface,
wherein the upper portion is thicker than the lower portion.

2. The medical knife of claim 1, wherein the second slanting surface has a non-reflective surface having a plurality of concavities and convexities formed therein.

3. The medical knife of claim 1, wherein the upper portion has a thickness of 55% to 99% of the thickness of the medical knife.

4. The medical knife of claim 1, wherein the upper portion has a thickness of 75% to 99% of the thickness of the medical knife.

* * * * *